(12) United States Patent
Washington et al.

(10) Patent No.: US 7,074,218 B2
(45) Date of Patent: Jul. 11, 2006

(54) MULTI-MODALITY ABLATION DEVICE

(75) Inventors: Ebonia Washington, Edison, CT (US); Jonathan Kwok, Somerset, NJ (US); Vaclav O. Podany, New Fairfield, CT (US); Rajesh Pendekanti, Bridgewater, NJ (US)

(73) Assignee: Ethicon, Inc., Somerville, NJ (US)

( * ) Notice: Subject to any disclaimer, the term of this patent is extended or adjusted under 35 U.S.C. 154(b) by 156 days.

(21) Appl. No.: 10/609,694

(22) Filed: Jun. 30, 2003

(65) Prior Publication Data
US 2004/0267252 A1    Dec. 30, 2004

(51) Int. Cl.
*A61B 18/18* (2006.01)
*A61B 8/00* (2006.01)

(52) U.S. Cl. .......................... 606/41; 606/27; 600/439

(58) Field of Classification Search ................. 606/27, 606/28, 41; 604/22; 600/437, 439, 459, 600/462, 466; 601/2, 3
See application file for complete search history.

(56) References Cited

U.S. PATENT DOCUMENTS

| | | | | |
|---|---|---|---|---|
| 4,936,281 A | * | 6/1990 | Stasz | 600/439 |
| 5,013,312 A | * | 5/1991 | Parins et al. | 606/37 |
| 5,282,799 A | * | 2/1994 | Rydell | 606/48 |
| 5,295,484 A | * | 3/1994 | Marcus et al. | 600/439 |
| 5,893,848 A | * | 4/1999 | Negus et al. | 606/41 |
| 6,235,024 B1 | * | 5/2001 | Tu | 606/41 |
| 2004/0116921 A1 | | 6/2004 | Sherman et al. | |

* cited by examiner

*Primary Examiner*—Michael Peffley

(57) ABSTRACT

An instrument for ablation of tissue. The instrument including: a body having at least one surface for contacting a tissue surface, the at least one surface being substantially planar; an ultrasonic transducer disposed in the body for generating ultrasonic energy and directing at least a portion of the ultrasonic energy to the tissue surface, the ultrasonic transducer being operatively connected to an ultrasonic generator; at least one radio-frequency electrode disposed on the at least one surface for directing radio frequency energy to the tissue surface, the at least one radio-frequency electrode being operatively connected to a power source; and one or more switches for selectively coupling at least one of the ultrasonic transducer to the ultrasonic generator and the at least one radio-frequency electrode to the power source.

8 Claims, 3 Drawing Sheets

MULTI-MODALITY ABLATION DEVICE

BACKGROUND OF THE INVENTION

1. Field of the Invention

The present invention relates generally to medical instrumentation, and more particularly, to a multi-modality ablation device.

2. Prior Art

Ultrasonic and radio frequency instruments are well known in the medical arts. Such instrumentation may be used to make lesions in tissue, but are also used to cut and coagulate tissue and blood, respectively. Typically, ultrasonic instrumentation has an ultrasonic transducer at a working end of the instrument, while radio frequency instruments have one or more electrodes at a working end of the instrument. Each of the working ends is typically separated from a handle or other manipulation means by an elongated shaft.

Instruments utilizing radio frequency energy perform well for single-sided ablation of thin tissue. However, this modality can only ablate thicker tissue at the expense of lesion width. Creating wider lesions with radio frequency energy may result in damage to critical peripheral tissue structures. Beyond 6 mm in tissue depth, radio frequency energy may not achieve lesion transmurality. On the other hand, instruments utilizing ultrasound energy perform well for thick tissue ablation because the energy can be focused into the depth of the tissue. However, for thin tissue, ultrasound may be ineffective as the ultrasound energy is focused in blood, not in the tissue.

Thus, the surgeon must determine the efficacy of the lesion created with one of the ultrasound or radio frequency instruments and may need to exchange instrumentation to create a proper lesion, all of which significantly increase the time of the procedure (ablation cycle time).

SUMMARY OF THE INVENTION

Therefore it is an object of the present invention to provide ablation devices and methods for their use that overcome the disadvantages of conventional instrumentation known in the art.

Accordingly, the devices and methods of the present invention utilize one or both ultrasound and radio frequency energy modalities to achieve an efficacious lesion with minimum activation time. Thus, ablation cycle time and adverse effects such as excessive peripheral thermal damage to tissue are minimized when the modalities are used together, when necessary.

Therefore, an instrument for ablation of tissue is provided. The instrument comprising: a body having at least one surface for contacting a tissue surface, the at least one surface being substantially planar; an ultrasonic transducer disposed in the body for generating ultrasonic energy and directing at least a portion of the ultrasonic energy to the tissue surface, the ultrasonic transducer being operatively connected to an ultrasonic generator; at least one radio-frequency electrode disposed on the at least one surface for directing radio frequency energy to the tissue surface, the at least one radio-frequency electrode being operatively connected to a power source; and one or more switches for selectively coupling at least one of the ultrasonic transducer to the ultrasonic generator and the at least one radio-frequency electrode to the power source.

The body can comprise a non-conductive head, the non-conductive head having a cavity for housing the ultrasonic transducer. The head can further have a heat exchanger for cooling at least one of the ultrasonic transducer, the at least one radio-frequency electrode, and the tissue surface. The at least one radio-frequency electrode can comprise first and second radio-frequency electrodes, the first radio-frequency electrode being maintained at a first polarity and the second radio-frequency electrode being maintained at a second polarity different from the first polarity. The first and second radio frequency electrodes can comprise first and second conductive surfaces, respectively, disposed on the non-conductive head. The first and second conductive surfaces can be separated by the cavity and the cavity can be enclosed with an acoustic window on the at least one surface.

Also provided is an instrument for ablation of tissue where the instrument comprises: an ultrasonic transducer for generating ultrasonic energy and directing at least a portion of the ultrasonic energy to a tissue surface; and at least one radio-frequency electrode for directing radio frequency energy to the tissue surface, the at least one radio frequency electrode being disposed substantially in a plane with the ultrasonic transducer.

The instrument can further comprise one or more switches for selectively powering at least one of the ultrasonic transducer and the at least one radio-frequency electrode.

Still provided is a system for ablation of tissue, where the system comprises: a tissue thickness measurement means for measuring a thickness of tissue corresponding to a tissue surface to be ablated; and an instrument having an ultrasonic transducer for generating ultrasonic energy and directing at least a portion of the ultrasonic energy to the tissue surface; at least one radio-frequency electrode for directing radio frequency energy to the tissue surface; and one or more switches for selectively powering at least one of the ultrasonic transducer and the at least one radio-frequency electrode based on the measured tissue thickness.

The system can further comprise an ultrasonic generator selectively coupled to the ultrasonic transducer by the one or more switches. The system can also further comprise a power source selectively coupled to the at least one electrode by the one or more switches.

Still provided is a method for creating lesions in tissue. The method comprising: providing an instrument capable of selectively directing at least one of ultrasonic and radio-frequency energy to the tissue; measuring a tissue thickness corresponding to the tissue; and applying at least one of ultrasonic and radio-frequency energy from the instrument to the tissue based on the measuring.

The applying can comprise applying the ultrasonic and radio-frequency energy from the instrument to the tissue surface where the measured tissue thickness is greater than a first predetermined thickness. The first predetermined thickness can be about 6 mm.

The applying can comprise applying only the radio-frequency energy from the instrument to the tissue surface where the measured tissue thickness is less than a second predetermined thickness. The second predetermined thickness can be about 3–5 mm.

The applying can comprise applying only the ultrasonic energy from the instrument to the tissue surface where the measured tissue thickness is between the first predetermined thickness and the second predetermined thickness.

Where the ultrasonic energy is supplied by an ultrasonic transducer and the radio-frequency energy is supplied by at least one electrode, the method can further comprise cooling at least one of the ultrasonic transducer, the at least one electrode, and the tissue.

Still provided is a method for creating lesions in tissue where the method comprises: measuring a tissue thickness corresponding to the tissue; and applying ultrasonic and radio-frequency energy to the tissue surface where the tissue thickness is greater than a predetermined thickness.

The applying can comprise applying the ultrasonic energy followed by applying the radio-frequency energy.

Still yet provided is a method for creating lesions in tissue where the method comprises: measuring a tissue thickness corresponding to the tissue; applying ultrasonic energy to the tissue surface to create a lesion where the tissue thickness is greater than a predetermined thickness; determining an extent of the lesion created by the applying of the ultrasonic energy; and applying radio-frequency energy to the tissue surface where the extent of the lesion is determined to be unsatisfactory.

BRIEF DESCRIPTION OF THE DRAWINGS

These and other features, aspects, and advantages of the apparatus and methods of the present invention will become better understood with regard to the following description, appended claims, and accompanying drawings where:

DETAILED DESCRIPTION OF THE PREFERRED EMBODIMENT

Figure 1:
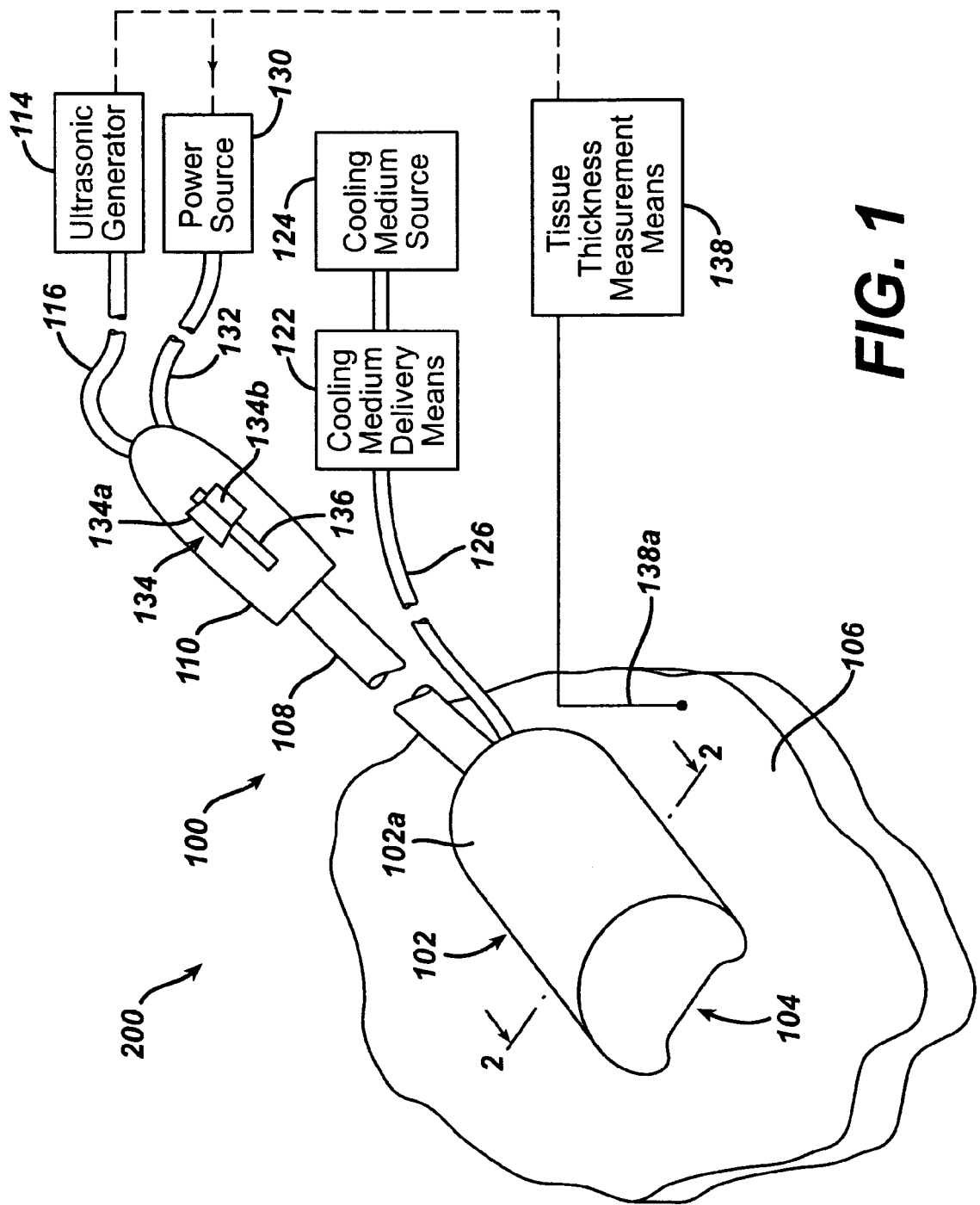
FIG. 1 illustrates a perspective view of a system for ablating tissue having an embodiment of a tissue ablation instrument according to the present invention.
Figure 2:
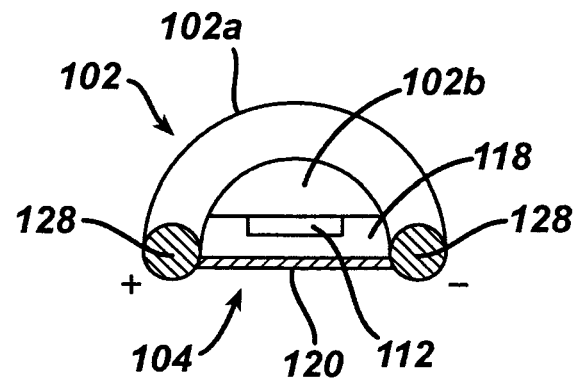
FIG. 2 illustrates a sectional view of the instrument of FIG. 1 as taken along line 2—2 of FIG. 1.
Figure 3:
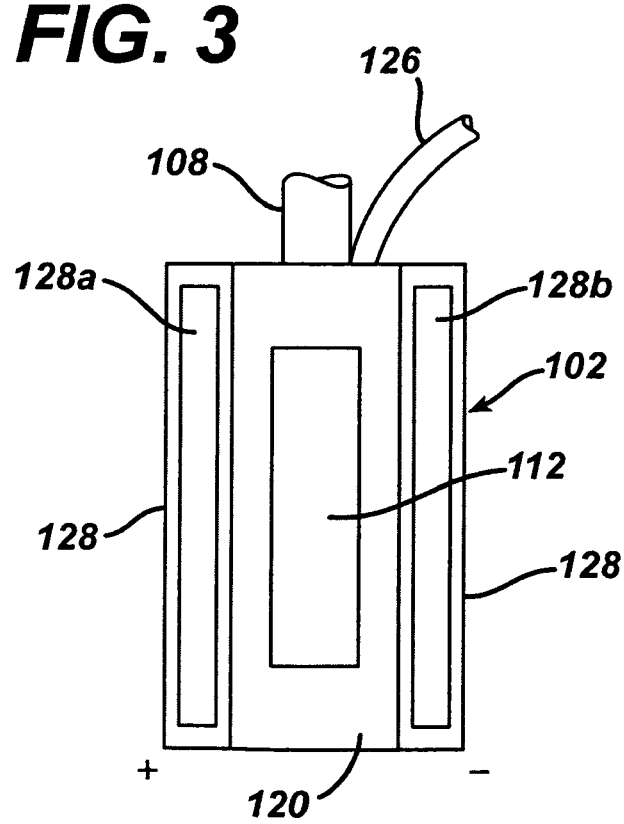
FIG. 3 illustrates a partial bottom view of the instrument of FIG. 1.

Referring now to FIGS. 1–3, therein is illustrated an instrument and system for ablation of tissue, the instrument generally referred to by reference numeral 100 and the system generally referred to by reference numeral 200. Although the instrument 100 is shown and described as a rigid instrument, it can also be configured in other ways without departing from the scope or spirit of the present invention. For example, the instrument 100 may be configured as a catheter, a minimally invasive instrument, or a less invasive instrument. The instrument 100 has a body 102 having at least one surface 104 for contacting a tissue surface 106. The surface is substantially planar, but may be slightly curved to follow a contour of a curved tissue surface. The body 102, as configured by way of example only, is disposed at a distal end of an elongated tube 108. The elongated tube 108 has a handle 110 disposed at a proximal end thereof. The body 102 preferably comprises a non-conductive head 102a.

The body 102 has a cavity 102b for housing at least one ultrasonic transducer 112 for generating ultrasonic energy and directing at least a portion of the ultrasonic energy to the tissue surface 106. The ultrasonic transducer 112 is operatively connected to an ultrasonic generator 114, preferably by wiring 116. The wiring 116 is preferably connected, either hardwired to the handle 110 or through a releasable connector (not shown) on the handle 110 and is routed to the ultrasonic transducer 112 through the elongated tube 108. The wiring 116 may also be routed externally to the handle 110 and/or elongated tube 108. Alternatively, the ultrasonic generator may be integrally formed in the instrument 100, such as in the handle 110. The ultrasonic transducer 112 is fixed in the body 102 by any means known in the art, such as with a bracket or epoxy 118. An acoustic window 120 fabricated from a material which transmits ultrasonic energy encloses the cavity on the at least one surface 104.

The body 102 and/or ultrasonic transducer 112 can be configured in any way known in the art for creating lesions in tissue, such as that disclosed in co-pending U.S. application Ser. No. 10/675,891 entitled System For Creating Linear Lesions for the Treatment of Atrial Fibrillation, the entire contents of which is incorporated herein by its reference. For example, the ultrasonic transducer 112 can be convexly curved such that the resulting ultrasonic energy is focused along a straight or curved line along the length of the ultrasonic transducer 112 to create a lesion. The ultrasonic transducer 112 may also have an impedance matching coating (not shown) on the side of the ultrasonic transducer 112 that faces the acoustic window 120. The ultrasonic transducer 112 can further provide for circulation of a cooling medium, such as a fluid, through the cavity 102b. The cooling medium, for example, water or saline, may be re-circulated through the cavity 102b or through other openings (not shown) in the body 102 from a cooling medium delivery means 122, such as a pump or a syringe. The cooling medium delivery means 122 can draw cooling medium from a cooling medium source 124 and deliver the same to the instrument 100 by way of tubing 126. The tubing 126 can be routed externally to the handle 110 and elongated tube 108, as shown in FIG. 1, or routed internally to the handle 110 and elongated tube 108. In any configuration, the cooling medium is directed to the cavity 102b and may be dumped thereafter or re-circulated. The cooling medium acts as a heat exchanger for cooling the ultrasonic transducer 112 but may also cool the radio-frequency electrode(s) (discussed below) and the tissue surface (106). The ultrasonic transducer 112 can also be positioned in the cavity 102b such that an air gap exists between a back surface of the ultrasonic crystal and a front surface of the cavity 102b. The configuration of the ultrasonic transducer 112 is given by way of example only and not to limit the spirit or scope of the present invention. Those skilled in the art will appreciate that the ultrasonic transducer 112 can be configured in any manner known in the art for producing ultrasonic energy for its intended purpose.

The instrument 100 further has at least one radio-frequency electrode 128 disposed on the at least one surface of the body 102 for directing radio frequency energy to the tissue surface 106. The at least one radio frequency electrode 128 is preferably disposed substantially in a plane with the ultrasonic transducer 112. The radio-frequency electrode(s) 128 are operatively connected to a power source 130, such as an electro-surgical unit, by way of wiring 132. The wiring 132 can be hardwired to the instrument 100 or releasably connected by way of a connector (not shown). Furthermore, the wiring 132 can be routed internally in the handle 110 and/or elongated tube 108, as shown in FIG. 1, or external thereto. The radio-frequency electrode(s) 128 can be configured as monopolar or bipolar as is known in the art of electro-surgical instrumentation. In a monopolar configuration, one or more electrodes are at a first polarity and when energized, current flows through the patient and exits through a ground plate attached to the patient. In a bipolar configuration, as shown in FIG. 2, two or more radio-frequency electrodes 128 are utilized, a first radio-frequency electrode 128 is maintained at a first polarity (+) and a second radio-frequency electrode 128 is maintained at a second polarity (−) different from the first polarity (+). In such a configuration, the first and second radio-frequency electrodes are arranged in a side-by-side relationship with the transducer 112, with the transducer preferably being positioned in between the first and second radio-frequency electrodes 128 in a substantially planar configuration. In the bipolar configuration, current flows from one electrode to the other, thus, the need for a grounding plate is eliminated. As shown in FIGS. 2 and 3, the two electrodes 128 are separated by the cavity 102b. The two radio-frequency electrodes 128 preferably are first and second conductive surfaces 128a, 128b, respectively, disposed on the non-conductive head 102a. However, the head 102a may also be conductive and coated with a non-conductive coating in all portions except the first and second conductive surfaces.

The instrument 100 further has one or more switches 134 for selectively coupling the ultrasonic transducer 112 to the ultrasonic generator 114 and the radio-frequency electrode(s) 128 to the power source 130. The switches 134a, 134b can be integral with the instrument 100, such as formed on the handle 110 as shown in FIG. 1, or remote therefrom, such as a footswitch (not shown) or a switch located on the external wiring 116, 132, as are known in the art. Preferably, the switches 134 comprise a split switch having first and second buttons 134a, 134b each of which can be operated independently, by sliding one or both in a slot 136 formed in the handle 110.

The system can also include a tissue thickness measurement means 138 for measuring a thickness of tissue corresponding to the tissue surface 106 to be ablated. An imaging modality, such as ultrasound imaging, or other measurement, such as electrical characteristics, can be used to determine the tissue thickness. Tissue thickness measurement is well known in the art, such as that disclosed in U.S. Pat. No. 6,524,250, the entire contents of which is incorporated herein by its reference. In FIG. 1, the probe 138a is meant to schematically illustrate structure, such as an ultrasound transducer, for measuring tissue thickness, such as that disclosed in U.S. Pat. No. 6,524,250. Although the tissue thickness measurement means 138 is shown separate from the instrument 100, the same can also be integrally formed with the instrument 100 and may even utilize the radio-frequency electrode(s) 128 and/or ultrasonic transducer 112 for such purposes. Furthermore, as discussed below, the mode of operation of the instrument 100 can depend upon the thickness of the tissue corresponding to the tissue surface 106 to be ablated. Thus, the tissue thickness measurement means 138 may output a value to the user of the instrument 100 and the user manually select a mode of operation based thereon. Alternatively, the tissue thickness measurement means 138 can automatically input one or both of the ultrasonic generator 114 and power source 130 (either directly (shown by dashed lines) or through a common processor-not shown) and control the same to automatically select a mode of operation.

Figure 4A:
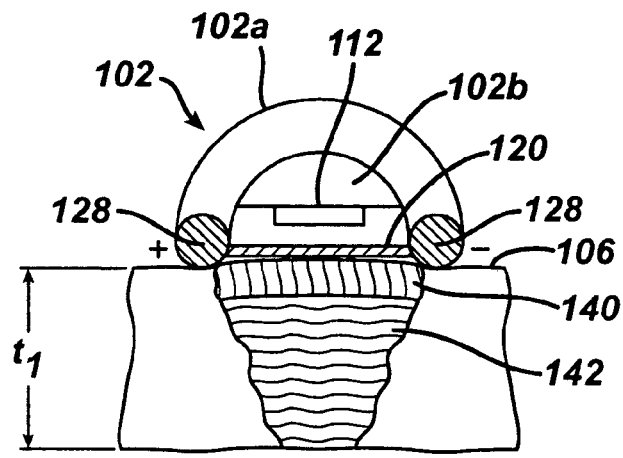
FIGS. 4a–4c illustrate creation of lesions with the instrument of FIG. 2 in tissue of varying thickness.
Figure 4B:
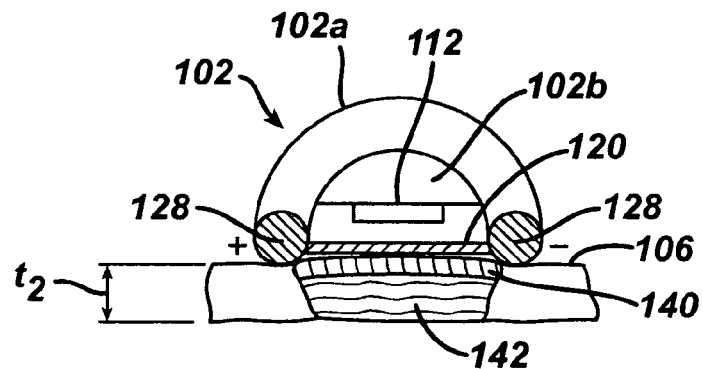
Figure 4C:
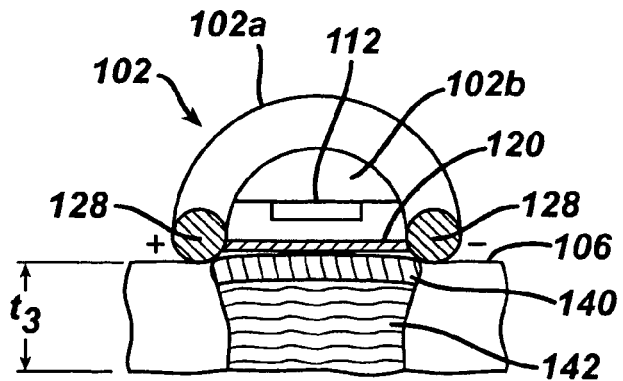

The operation and use of the instrument 100 and system 200 will now be described with regard to FIGS. 1–3 as well as FIGS. 4a–4c. The tissue surface 106 is first accessed by any means known in the art and the surface 104 of the body 102 is positioned over the tissue surface 106 to be ablated. The thickness of the tissue corresponding to the tissue surface 106 is then measured either manually by a user or automatically with the tissue thickness measurement means 138. At least one of ultrasonic and radio-frequency energy from the instrument 100 is then applied to the tissue surface 106 based on the measured thickness. As discussed above, the user may manually select one or both of the ultrasound energy or radio frequency energy through switches 134a, 134b or the system may automatically choose one or both of the ultrasound energy or radio frequency energy based on the measured thickness. In FIGS. 4a–4c, the lesion created by the ultrasonic energy is referred to by reference numeral 142 while the lesion created with radio frequency energy is referred to by reference numeral 140.

As shown in FIG. 4a, both the ultrasonic and radio frequency energy can be applied from the instrument 100 to the tissue surface 106 where the measured tissue thickness is greater than a first predetermined thickness $t_1$. The first predetermined thickness $t_1$ is preferably about 6 mm. In this case the focal spot of the ultrasonic energy is located in the tissue, which leads to most efficient heating of the tissue because heat is conducted to other areas of the tissue from the focal spot. As the tissue is ablated by the ultrasonic energy, it becomes more opaque to ultrasound, heating more on a side of the tissue closer to the ultrasonic transducer. Concurrently energy from the ultrasonic beam is absorbed as it is transmitted through the tissue so the tissue will heat more from the focal point to the transducer and will fill a "wedge-shaped lesion" when a focused ultrasound transducer is used. Preferably, the ultrasonic transducer is in direct contact with the tissue surface. Since the ultrasonic transducer is preferably cooled, it acts as a heat sink on the tissue surface. The tissue in contact with the ultrasonic transducer has a relatively small energy input because the ultrasonic beam is not focused there and the intensity is low. As a result, approximately the last ¼ to ½ mm of tissue on the surface is sometimes not sufficiently ablated. Thus, radio-frequency energy can be applied to ablate the top portion of the tissue (if the surgeon decides that it is necessary).

As shown in FIG. 4b, the measured tissue thickness is less than a second predetermined thickness $t_2$. The second predetermined thickness $t_2$ is about 3–5 mm. In this case the tissue is relatively thin and ablating using only ultrasound is not the most efficient because the beam is not focused in the tissue. Therefore, radio-frequency energy is used to speed up the ablation process and also to ablate the upper portion of the tissue, e.g., the upper 0.5 mm of the tissue. However, only the radio-frequency energy may also be used to ablate thin tissue.

As shown in FIG. 4c, the measured tissue thickness $t_3$ is between the first predetermined thickness and the second predetermined thickness. Thus, in moderately thick tissue, the focal spot of the ultrasonic energy may still be outside of the tissue, so the efficient heating mechanism discussed above may be missing and the conduction mechanism discussed above is minimized. Therefore, ablation of the tissue can be provided by a somewhat focused ultrasonic beam and radio-frequency energy can be applied to speed up the ablation process. However, in moderately thick tissue, only the ultrasonic energy may be applied to create an efficacious lesion.

Therefore, in all three cases discussed above, ultrasonic energy can be used to create a lesion in tissue, however, the use of radio-frequency energy in combination with the ultrasonic energy provides a good visual indication of the lesion created for the surgeon, both in terms of the location of the lesion and whether there is a gap in the lesion at the tissue surface. The imaging modality or other measurement such as electrical characteristics used for measuring tissue thickness can also be used to determine an extent of the lesion 142 created by applying the ultrasonic energy. Where the extent of the lesion 142 is determined to be unsatisfactory, the instrument can also apply radio-frequency energy to the tissue surface 106 until it is determined that the extent of the lesion is satisfactory.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. An instrument for ablation of tissue, the instrument comprising:
a body having at least one surface for contacting a tissue surface, the at least one surface being substantially planar, and a heat exchanger;
an ultrasonic transducer disposed in the body for generating ultrasonic energy and directing at least a portion of the ultrasonic energy to the tissue surface, the ultrasonic transducer being operatively connected to an ultrasonic generator;
at least one radio-frequency electrode disposed on the at least one surface for directing radio frequency energy to the tissue surface, the at least one radio-frequency electrode being operatively connected to a power source;
a tissue thickness measuring means for measuring a thickness of the tissue to be ablated; and
one or more switches for selectively coupling at least one of the ultrasonic transducer to the ultrasonic generator and the at least one radio-frequency electrode to the power source based on a measured thickness of the tissue, wherein the heat exchanger cools at least one of the ultrasonic transducer, the at least one radio-frequency electrode, and the tissue surface.

2. The instrument of claim 1, wherein the body comprises a non- conductive head, the non-conductive head having a cavity for housing the ultrasonic transducer.

3. The instrument of claim 2, wherein the at least one radio-frequency electrode comprises first and second radio-frequency electrodes, the first radio-frequency electrode being maintained at a first polarity and the second radio-frequency electrode being maintained at a second polarity different from the first polarity.

4. The instrument of claim 3, wherein the first and second radio frequency electrodes comprises first and second conductive surfaces, respectively, disposed on the non-conductive head.

5. The instrument of claim 4, wherein the first and second conductive surfaces are separated by the cavity.

6. The instrument of claim 2, wherein the cavity is enclosed with an acoustic window on the at least one surface.

7. An instrument for ablation of tissue, the instrument comprising:
a tissue thickness measuring means for measuring a thickness of the tissue to be ablated;
an ultrasonic transducer for generating ultrasonic energy and directing at least a portion of the ultrasonic energy to a tissue surface based on the measured thickness of the tissue;
at least one radio-frequency electrode for directing radio frequency energy to the tissue surface based on the measured thickness of the tissue, the at least one radio frequency electrode being disposed substantially in a plane with the ultrasonic transducer; and
a heat exchanger for cooling at least one of the ultrasonic transducer, the at least one radio-frequency electrode, and the tissue surface.

8. The instrument of claim 7, further comprising one or more switches for selectively powering at least one of the ultrasonic transducer and the at least one radio-frequency electrode.

* * * * *